United States Patent [19]

Bloch

[11] Patent Number: 4,788,180

[45] Date of Patent: Nov. 29, 1988

[54] PHARMACEUTICAL COMPOSITIONS

[76] Inventor: Maurice Bloch, 4 Lansdowne Road, London, N3 1ES, United Kingdom

[21] Appl. No.: 675,900

[22] PCT Filed: Mar. 26, 1984

[86] PCT No.: PCT/GB84/00099

§ 371 Date: Nov. 26, 1984

§ 102(e) Date: Nov. 26, 1984

[87] PCT Pub. No.: WO84/03623

PCT Pub. Date: Sep. 27, 1984

[30] Foreign Application Priority Data

Mar. 24, 1983 [GB] United Kingdom ............... 8308126

[51] Int. Cl.$^4$ .................. A61K 9/22; A61K 33/08; A61K 33/06

[52] U.S. Cl. ................................. 514/26; 514/474; 514/819; 514/869; 424/153; 424/154; 424/156; 424/476

[58] Field of Search ............. 424/153, 154, 156, 476; 514/26, 474, 819, 869

[56] References Cited

U.S. PATENT DOCUMENTS

| 3,843,778 | 10/1974 | Diamond et al. | 514/819 |
| 4,104,370 | 8/1978 | Bloch | 424/153 |
| 4,150,111 | 4/1979 | Warren et al. | 424/153 |
| 4,421,743 | 12/1983 | Alvarez | 424/154 |
| 4,446,135 | 5/1984 | Fountaine | 424/154 |
| 4,533,543 | 8/1985 | Morris et al. | 424/154 |

FOREIGN PATENT DOCUMENTS 4265M 8/1966 France .
1422193 1/1976 United Kingdom .

Primary Examiner—Ronald W. Griffin
Attorney, Agent, or Firm—Watson, Cole, Grindle & Watson

[57] ABSTRACT

A pharmaceutical composition comprises magnesium oxide, hydroxide or a non-toxic salt of magnesium in a slow-release carrier; this material may be combined with or co-prescribed with a diuretic or cardiac glycoside or adrenergic receptor blocking agent or a calcium antagonist for the treatment of hypertension or angina pectoris.

13 Claims, No Drawings

PHARMACEUTICAL COMPOSITIONS

BACKGROUND OF THE INVENTION

This invention relates to pharmaceutical compositions comprising magnesium compounds.

In man and in animals (see Williams RJP, Wacker WEC, Cation Balance in Biological Systems, J. Amer. Med. Ass. 1967; 201/1: 96–100) intracellular concentrations of the four principal cations, sodium, potassium, magnesium and calcium, are in equilibrium such that log concentration ratios of the divalent cations magnesium and calcium are directly related to those for the monovalent cations potassium and sodium: total intracellular concentrations of sodium plus potassium and of magnesium plus calcium are respectively similar to those in extracellular fluid, and thus are similar on both sides of the cell membrane.

In man and in animals (Bloch M., Magnesium Depletion: Possible Significance in Ischaemic Heart Disease, Brit. J. Hosp. Med. 1973; 91–98) magnesium depletion results in negative magnesium and potassium balance, and positive sodium, calcium, and water balance; in intracellular loss of magnesium and potassium, and gain in sodium and calcium; in increase in extracellular fluid space; and in hypomagnesaemia, hypokalaemia, and hypocalcaemia. All these changes are reversible with I have postulated that normal vascular muscle tone, a major determinant of normal blood pressure, is critically dependent on cation balance; that magnesium plays a signficiant role in blood pressure control; and that cation imbalance resulting from magnesium depletion, leading to relative and absolute increase in intracellular and total body calcium and sodium, and to decrease in intracellular and total body magnesium and potassium, would be expected to result in increase in vascular muscle tone and in blood pressure. In support of this hypothesis, it was noted also that magnesium depletion has been observed in association with increase in renal, cardiac, and skeletal-muscle calcification in animals, and that increase in myocardial calcium content has been reported in magnesium-deficient hearts of patients with ischaemic heart disease.

Further support for this hypothesis comes from recent observations in normal subjects and in patients with essential hypertension, linking increase in blood pressure to change in cation balance, these indicating variously (see Editorial. Essential hypertension: another defect? Lancet 1980; i: 1227–29.

Editorial. Cells, ions, and blood pressure. Lancet 1982; ii: 965–967.

Lever AF, Beretta-Piccoli C, Brown JJ, Davies DL, Fraser R, Robertson JIS. Sodium and potassium in essential hypertension. Brit. Med. J. 1981; 283: 463–468)

that blood pressure correlates positively with intracellular and total-body sodium content, and negatively with total-body potassium, plasma potassium concentration, and cellular efflux-rate of sodium; and that increase in blood pressure can be produced by increase in dietary sodium, and decrease in blood pressure by increase in dietary potassium (see Holly JMP, Goodwin FJ, Evans SJW, Vandenburg MJ, Ledingham JM. Re-analysis of data in two Lancet papers on the effect of dietary sodium and potassium on blood pressure. Lancet 1981; ii: 1384–87.

Khaw KT, Thom S. Randomised double-blind crossover trial of potassium on blood pressure in normal subjects. Lancet 1982; ii: 1127–29.

MacGregor GA, Smith SJ, Markandu ND, Banks RA, Sagnella GA. Moderate potassium supplementation in essential hypertension. Lancet 1982; ii: 567–570.).

In dogs given intravenous solutions producing hypokalaemia, hypomagnesaemia, and hypokalaemia, alone and in combination, mean systolic and diastolic blood pressure increased; local hypermagnesaemia is associated with decrease in resistance in forelimb, kidney, coronary, gastric, mesenteric and hepatic vascular beds in the dog and in the human forearm (see Emerson, TE, Scott JB, Haddy FJ., Effects of acute multiple changes in plasma electrolyte levels on dog blood pressure., Am. J. Physiol. 1970; 218/1: 234–240). In cats treated intravenously with magnesium, resultant fall in heart rate and in diastolic and systolic blood pressure were dose-dependent and correlated negatively with plasma magnesium concentration (see Ebel H, Classen HG, Marquardt P, Spaeth M., Zur Pharmakologie und Pharmakokinetik von Magnesium, Muench. Med. Wochenschr. 1975; 117/29–30: 1243–48). It is argued in the Editorial in Lancet 1982; ii: 965–967, cited above, that increase in vascular muscle tone might result from increase in free intracellular calcium; that abnormality of sodium transport does not have a primary role in genesis of essential hypertension; and that cation changes observed in essential hypertension reflect an unidentified underlying abnormality, the so-called "innocent bystander".

These changes can all be produced by withdrawing dietary magnesium and reversed by magnesium repletion, and are compatible with the view that the reported abnormalities of sodium transport do not have a primary role in genesis of raised blood pressure in essential hypertension.

Since magnesium depletion might be widespread in Westernised communities (see Bloch M. Brit. J. Hosp. Med. 1973; 91–98 cited above), this might constitute a significant factor in the genesis of essential hypertension, and therefore treatment with magnesium might contribute to control of blood pressure in patients with this condition.

It is known that, when certain pharmaceutical compositions, in particular certain diuretics, are used, they cause loss of magnesium and potassium from the body. Toxicity of other pharmaceutical compositions, in particular of cardiac glycosides, is increased by potassium and magnesium depletion. Diuretics and cardiac glycosides are frequently prescribed for the same patient, and it is a known practice to administer also a potassium salt, e.g., potassium chloride, which might be given in a slow release preparation.

However, administration of potassium might give rise to unwanted side effects, e.g., vasoconstriction and gastric ulceration.

In particular, experimentally, these side effects can be prevented by magnesium ions, which have vasodilator activity, provided concentration of magnesium ions (m.eq./l.) exceeds that of potassium ions. Hence it has been proposed in U.K. Patent Specification No.1422193 and in U.S. Pat. No. 4,104,370 to provide a pharmaceutical composition comprising magnesium oxide, magnesium hydroxide, or a non-toxic pharmaceutically acceptable salt of magnesium in combination with a nontoxic pharmaceutically acceptable salt of potassium, the equivalent weight of magnesium being between 1 and 3, and preferably between 1 and 2 times the equivalent weight of the potassium, together with a pharmaceutical carrier, such that the rate of release of the magnesium and the rate of release of the potassium into the digestive system is controlled. Such a material may be co-prescribed or combined with a diuretic or cardiac glycoside.

Therapeutic usefulness of magnesium is limited by its action on the gut, causing purgation, unless administered in comparatively small doses. This limitation is overcome, in the use of the above-described composition, by the employment of a controlled-release preparation so that the magnesium is administered in therapeutically meaningful dosages.

SUMMARY OF THE INVENTION

In the present application, it is proposed that, although loss of magnesium from the body might be associated with loss of potassium (arising for example from action of a diuretic), combined administration of magnesium and potassium is mostly not necessary for control of magnesium and potassium loss from the body; administration of magnesium alone serves not only to replace magnesium lost from the body but also to conserve body potassium.

According to the present invention, a pharmaceutical composition comprises magnesium oxide, magnesium hydroxide or a non-toxic pharmaceutically acceptable salt of magnesium, together with a pharmaceutically acceptable carrier, such that the rate of release of the magnesium into the digestive system is controlled. The controlled release might typically be made to give a duration of action in the range 2 to 24 hours.

In accordance with the present invention, it is proposed that magnesium compounds, e.g. magnesium oxide or hydroxide or salts are used in prophyalxis and treatment of potassium depletion in patients treated long-term with diuretic agents; in other conditions associated with potassium depletion, e.g., cardiac ischaemia, chronic cardiac failure, malabsorption, etc); concommitantly with treatment with cardiac glycosides; and also in treatment of essential hypertension.

More particularly, since cation changes correlating with increase in blood pressure, experimentally and in essential hypertension, namely, increase in intracellular and total-body sodium and in extracellular fluid space, and decrease in sodium efflux rate, in total-body potassium, and in plasma concentrations of magnesium, potassium, and calcium, can all be produced by withdrawing dietary magnesium and can be reversed with magnesium replenishment, coprescription of magnesium together with diuretic agents and/or adrenergic receptor blocking agents will augment control of blood pressure obtained with these agents; alternatively, magnesium compositions might be used alone in treatment of essential hypertension.

Coprescription of diuretic agents with magnesium, which has a significant role in conserving wholebody and intracellular potassium, will act additionally to prevent or reduce potassium depletion resulting from increased renal loss of potassium and magnesium in patients treated long-term with diuretic agents, and of potassium in patients treated with $\beta$ adrenergic receptor blocking agents (see Steiness E., "Serum potassium and thiazide/beta - blocker combinations," Lancet 1982; i: 971/2).

Thus an improved method of treating magnesium/potassium depletion in man might comprise administering orally a pharmaceutical composition, in an effective amount of composition to produce the required activity, (in solid form) for oral administration via a controlled-release carrier, comprising magnesium oxide, magnesium hydroxide or a non-toxic pharmaceutically acceptable salt of magnesium, together with a pharmaceutical carrier such that the rate of release of the magnesium into the digestive system is controlled to reduce or minimize the purgative action of the magnesium. The release time is a minimum of 2 hours and may be up to 12 hours, but preferably is longer, for example up to 24 hours.

A magnesium compound might be co-prescribed with a diuretic or cardiac glycoside or might include the required dosage of diuretic or cardiac glycoside.

Dosage of magnesium will vary with degree of depletion; proposed unit dosage (per capsule, tablet, etc.) will provide on the order of 5 to 30 mg. equivalents of magnesium.

As previously explained, magnesium release into the gut must be controlled so as to limit purgative action, and to provide for magnesium to be administered in therapeutically meaningful dosages. Release of magnesium might be controlled, if required, so as not to coincide with that of a diuretic agent or cardiac glycoside with which it is combined or co-prescribed.

Thus according to one aspect of the present invention there is provided a pharmaceutical composition comprising magnesium oxide, magnesium hydroxide, or a nontoxic pharmaceutically acceptable salt of magnesium, together with a pharmaceutically acceptable carrier, such that the rate of release of the magnesium into the digestive system is controlled, in combination with a diuretic or cardiac glycoside.

According to another aspect of the present invention, there is provided a pharmaceutical composition comprising magnesium oxide, magnesium hydroxide, or a non-toxic pharmaceutically acceptable salt of magnesium, together with a pharmaceutically acceptable carrier, such that the rate of release of the magnesium into the digestive system is controlled, in combination with an adrenergic receptor blocking agent.

Preferably the magnesium is in the form of magnesium oxide, magnesium hydroxide, magnesium chloride, magnesium sulphate, magnesium gluconate or magnesium phosphate or a combination of these compounds. In some cases, however magnesium carbonate may be employed. Because of its high magnesium content, it is found that magnesium oxide is particularly useful. For this purpose any suitable controlled or sustained release formulation may be employed to obtain the required rate of release.

The principal effects of adrenergic receptor blocking agents include peripheral vasodilatation, reduction in cardiac rate and output leading to decrease in oxygen consumption, and a cell membrane stabilising effect. These are complementary to, or supplement, effects produced with magnesium, in particular vasodilatation, and the changes in cation balance referred to above. It is therefore appropriate for the magnesium compound and the adrenergic receptor blocking agent to be prescribed together, for example, in treatment of hypertension; angina pectoris (possibly via coronary artery vasodilatation, reduction in cardiac output and in oxygen consumption); cardiac arrhythmia (possibly via membrane stabilizing effect, intracellular potassium conservation), etc.

Examples of adrenergic receptor blocking agents with typical dosages are:

| | |
|---|---|
| oxprenolol | (20, 40 mg) |
| propranolol | (40, 80 mg) |
| pindolol | (5 mg) |
| sotalol | (40, 80 mg) |
| timolol | (10 mg) |
| nadolol | (40, 80 mg) |
| acebutolol | (100, 200 mg) |
| atenolol | (100 mg) |
| metoprolol | (50, 100 mg) |
| labetalol | (100, 200 mg) |
| prozasin | (0.5, 1, 2 5 mg). |

The invention includes within its scope an improved method of treatment by an adrenergic receptor blocking agent comprising administering orally a pharmaceutical composition, in an effective amount of composition to produce the required activity, comprising magnesium oxide, magnesium hydroxide or a non-toxic pharmaceutically acceptable sale of magnesium, together with the adrenergic receptor blocking agent. The magnesium compound may be co-prescribed with the adrenergic receptor blocking agent. Preferably the treatment is effected by oral administration, for example by capsule or tablet, of a combination of the adrenergic receptor blocking agent with the magnesium compound.

The magnesium compound, formulated for controlled release, also finds particular application combined with or co-prescribed with a calcium antagonist, such as nifedipine or verapamil, so as to enhance the effects of these latter drugs, via the whole body and intracellular effects described above and/or via reduction in peripheral and coronary vascular resistance and/or via a membrane stabilizing effect of magnesium, in treatment, for example, of angine pectoris and/or hypertension.

Any suitable controlled or sustained release formulation may be employed for the preparation of the compositions in order to obtain the required controlled rate of release into the digestive system. One type of such preparation is based on a plurality of small cores which may be themselves of an inactive material such as sugar, synthetic resin or naturally occurring seeds such as rape seeds. Particularly suitable are "nonpareil seeds" as used in the confectionery industry which comprise sugar crystals coated with starch, talc, kaolin and syrup. Alternatively, the cores may themselves be formed of the medicament to be administered. These cores are then coated with one or more layers of a material which dissolves at a slow but controlled rate in the gastrointestinal tract of the patient. Examples of such time-delay materials (which are described in greater detail hereinafter) include glyceryl monostearate and beeswax and since the latter is much less dispersible than the former, by carrying the relative amounts of these materials the rate of dissolution and so the rate of release of the medicament (which may be incorporated within the coating material, form the central core or be applied as a separate layer between the core and the coating material) can be controlled. The rate of release may also be varied by altering the thickness of the coating material applied. A plurality of coated cores are combined in a suitable form such as a capsule, a tablet (a binder may be required in this case) or a suspension in a liquid. By combining coated cores having different time release characteristics a continuing release of medicament over a period of many hours from administration may be achieved. It will be understood that, by including uncoated medicament in the composition, an immediate effect can also be attained. The rate of absorption of the medicament used is a further factor which must be considered, and medicaments which are absorbed slowly generally only require a thin protective coating.

Another type of controlled release formulation which may be used is that which is produced by a process involving microencapsulation techniques.

Other well known methods of preparing sustained release preparations may also be employed. For example, the magnesium compound may be dispersed in a molten wax and then spray congealed. Fine powders comprising the magnesium compound may be suspended in a tower and coated with time delay material. Those coated powders can then be suspended in a liquid or encapsulated. Sustained release granules may also be prepared and either tabletted or placed in a soft gelatine capsule. Tablets may also be prepared as sustained release layered tablets.

The time delay material is a substantially water insoluble material resistant to disintegration in the gastrointestinal tract and providing for a gradual release of the medicament in the tract. The time delay material may be, for example, a wax, a fatty acid, alcohol or ester, alone or an admixture thereof.

The wax may be paraffin wax; a petrolatum wax; a mineral wax such as ozokerite, ceresin, utah wax or montan wax; a vegetable wax such as, for example, carnauba wax, Japan wax, bayberry wax, flax wax; an animal wax such as, for example, spermaceti; or an insect wax such as beeswax, Chinese wax or shellac wax. Additionally, the wax material may be an ester of a fatty acid having from 12 to 31 carbon atoms and a fatty alcohol having from 12 to 31 carbon atoms, the ester having a carbon atom content of from 24 to 62, or a mixture thereof. Exemplary are myricyl palmitate, ceryl palmitate, ceryl cerotate, myricyl mellissate, stearyl palmitate, stearyl myristate, lauryl laurate.

The fatty acid may have from 10 to 22 carbon atoms and may be for example, decenoic, docosanoic stearic, palmitic, lauric or myristic acid.

The fatty alcohols may have from 10 to 36 carbon atoms and may be, for example, lauryl alcohol, cetyl, stearyl, myristyl, myricyl, arachyl, carnaubyl or ceryl alcohol.

The esters may be mono-, di- or triglyceryl esters formed from fatty acids having from 10 to 22 carbon atoms, such as, for example, glyceryl distearate, glyceryl tristearate, glyceryl monostearate, glyceryl dipalmitate, glyceryl tripalmitate, glyceryl monopalmitate, glyceryl dilaurate, glyceryl trilaurate, glyceryl monolaurate, glyceryl didocosanoate, glyceryl tridocosanoate, glyceryl monodocosanoate, glyceryl monocaprate, glyceryl dicaprate, glyceryl tricaprate, glyceryl monomyristate, glyceryl dimyristate, glyceryl trimyristate, glyceryl monodecenoate, glyceryl didecenoate, glyceryl tridenenoate, hydrogenated castor oil, hydrogenated peanut oil and hydrogenated coconut oil.

The preferred sustained release materials are hydrogenated castor oil, glyceryl monostearate, glyceryl distearate, 12-hydroxystearyl alcohol and microcrystalline wax.

As previously indicated, a diuretic or cardiac glycoside may be combined or co-prescribed with the magnesium composition.

Exemplary of diuretics in the compositions of this invention are carbonic anhydrase inhibitors, for example acetazolamide; benzothiadiazides, for example bendroflumethiazide, benzthiazide, hydrochlorothiazide, chlorothiazide, cyclopenthiazide and altrizide; benzensulfonamides for example, furosemide, mefruside, bumetanide; chlorthalidone, metolazone, xipamide, clopamide; and ethacryic acid. Exemplary of cardiac glycosides in the composition of this invention are digoxin, digitoxin and lanatoside C. The diuretic agents and cardiac glycosides are present in amounts effective to produce the diuretic and cardiotonic activity. The effective amounts of the abovementioned diuretics and cardiac glycosides are known to the art. The appropriate daily dose of diuretic agent and cardiac glycoside may be given in divided doses and may be administered in conjunction with tablets or capsules containing only a magnesium composition, and all made available in one presentation pack. The diuretic agent and cardiac glycoside may be present in the pharmaceutical formulation with or without means for controlling their release into the digestive system.

As previously explained, the magnesium compound may be co-prescribed with a diuretic or a cardiac glycoside and presented as a tablet, capsule, suspension, etc. Thus the invention furthermore includes within its scope a pharmaceutical composition for co-prescribing with a diuretic or cardiac glycoside for treating magnesium/potassium depletion in a human comprising magnesium oxide, magnesium hydroxide or a non-toxic pharmaceutically acceptable salt of magnesium together with a pharmaceutically acceptable carrier, for oral administration, the carrier being such that rate of release of magnesium into the digestive system is controlled so that duration of action of the composition is up to 24 hours. Use of such a co-prescribed compound thus gives freedom for adjusting the amount of magnesium taken relative to other medicaments.

The invention is illustrated but in no way limited by the following specific examples.

EXAMPLE 1

A mixture of magnesium oxide, a flowing agent such as fumed silicon dioxide, a disintegrant such as an alginate and starch or another pharmaceutical excipient to aid in disintegration and dispersion is milled and added to a tacky suspension of nonpareil seeds in an adhesive mixture comprising polyvinylpyrrolidone and a wetting agent dissolved in methylated spirits. When no more of the milled powder will adhere to the seeds, the coated pellets are dried by a stream of air and a further layer or coating applied by the same method. Finally, a protective coating of glycerol monostearate/beeswax is applied to the pellets, which now have a diameter of approximately 1 mm.

The pellets are filled into capsules such that each capsule contains 100 mg (5 milliequivalents) of magnesium oxide.

EXAMPLE 2

(a) A mixture of furosemide and a disintegrant such as starch is milled and added to a tacky suspension of nonpareil seeds in an adhesive mixture comprising gelatine in aqueous ethanol. When no more of the milled powder will adhere to the seeds, the coated pellets are dried by a stream of air and a further layer of coating applied by the same method. Finally a very thin coating of glycerol monostearate/beeswax is applied to the pellets.

(b) These pellets containing furosemide are mixed with pellets containing magnesium oxide described in Example 1 and filled into capsules or tablets in such proportions that each capsule or tablet contains for example 20 mg furosemide and 5 m.eq. magnesium oxide, or alternative quantities of these compounds.

EXAMPLE 3

Pellets containing
(a) hydroflumethiazide
(b) mefruside
(c) chlorthalidone
(d) clopamide
(e) hydrochlorothiazide
(f) methylclothiazide
(g) bendrofluazide
(h) bumetanide
(i) cyclopenthiazide
(j) ethacrynic acid
(k) metolazone
(l) acetazolamide are prepared by substituting the above compounds for furosemide in the procedure of Example 2a and these pellets are mixed with pellets containing magnesium oxide described in Example 1 and filled into capsules in such proportions that the capsules contain for example 5 m.eq. magnesium oxide, and
(a) 25 mg hydroflumethiazide
(b) 25 mg mefruside
(c) 25 mg chlorthalidone
(d) 20 mg clopamide
(e) 12.5 mg hydrochlorothiazide
(f) 5 mg methylclothiazide
(g) 2.5 mg bendrofluazide
(h) 1 mg bumetanide
(i) 0.25 mg cyclopenthiazide.
(j) 50 mg ethacrynic acid
(k) 5 mg metolazone
(l) 250 mg acetazolamide

EXAMPLE 4

Nonpareil seeds are coated with a mixture of digoxin and polyvinylpyrrolidone in ethanol, and the coated pellets are dried by a stream of air.

These pellets are mixed with pellets containing magnesium oxide as described in Example 1 and filled into capsules in such proportions that each capsule contains 0.25 mg digoxin and 5 m.eq. magnesium oxide.

The tablets or capsules of Examples 2, 3, and 4 contain a diuretic or a cardiac glycoside together with a magnesium compound. The capsules of Example 1 containing a magnesium compound are co-prescribed with a diuretic or a cardiac glycoside.

EXAMPLE 5

Magnesium oxide (5mEq) is combined with labetalol (100mg) or propranolol (80mg) or acebutolol (200mg). The combined material is made up into pellets each having a core of a nonpareil seed using a suitable adhesive mixture comprising polyvinyl pyrrolidone and a wetting agent dissolved in methylated spirits. The pellets are provided with a protective wax coating and filled into capsules containing the required dosage.

In some cases, it may be desirable, in the treatment of a patient, to co-prescribe or combine the magnesium compound not only with an adrenergic receptor blocking agent but also with a diuretic. Typical diuretics which may be employed are as follows:
  (a) hydroflumethiazide
  (b) mefruside
  (c) chlorthalidone
  (d) clopamide
  (e) hydrochlorothiazide
  (f) methylclothiazide
  (g) bendrofluazide
  (h) bumetanide
  (i) cyclopenthiazide
  (j) ethacrynic acid
  (k) metolazone
  (l) acetazolamide Such diuretics, when used, may cause loss of magnesium and potassium from the body. Although it is a known practice to administer also a potassium salt such as potassium chloride, which may be given in a slow release preparation, such administration of potassium is mostly inadequately effective in restoring normal body potassium content and may give rise to unwanted side effects such as vasoconstriction and gastric ulceration. Administration of magnenium may be employed not only to replace magnesium loss from the body but also to conserve body potassium.

It is well-known to co-prescribe adrenergic receptor blocking agents with diuretics. The present invention provides an improved method of treatment and pharmaceutical composition for such treatment in which magnesium oxide is administered with the adrenergic receptor blocking agent and diuretic thereby enhancing blood pressure control, and conserving body potassium.

An example of such a composition is as follows:

EXAMPLE 6

Magnesium oxide (5mEg) is combined with propranolol (80mg) plus hydrochlorotiazide (12.5, 25mg) or hydroflumethiazide (25mg) or bumeanide (1mg) or bendrofluazide (2.5, 5mg) or mefruside (25mg). The combined material is formed into pellets and made up into capsules in a similar manner to the material of the previously described Examples.

EXAMPLE 7

As previously mentioned, the magnesium, formulated for controlled release, may be combined or co-prescribed together with a calcium antagonist such as nifedipine or verapamil so as to enhance the effects of these latter drugs.

As an example, magnesium oxide (5mEq) is combined with nifedipine (5 or 10mg) or with verapamil (40 or 80 or 120 mg); the combined material being made up into capsules giving controlled release as in the previously described Examples.

These further combinations may be coprescribed or combined together with diuretic agents, as above, and/or together with adrenergic receptor blocking agents, as above, but adjusting dosages so as to provide for any additive or summation effects of these further combinations.

I claim:

1. A method of treating a human patient suffering from magnesium/potassium deficiency, said method comprising the step of orally administering to such human patient a therapeutically meaningful dosage of a pharmaceutical composition which consists essentially of a magnesium compound selected from the group consisting of magnesium oxide, magnesium hydroxide and pharmaceutically-acceptable salt of magnesium, and a pharmaceutically-acceptable carrier, said pharmaceutically-acceptable carrier functioning to control the release of magnesium into the digestive tract of said human patient over a period of from 2 to 24 hours.

2. A method as claimed in claim 1, wherein said pharmaceutically-acceptable salt of magnesium includes magnesium chloride, magnesium sulphate, magnesium gluconate, magnesium carbonate and magnesium phosphate.

3. A method as claimed in claim 1, wherein said pharmaceutical composition includes a diuretic agent.

4. A method as claimed in claim 1, wherein said pharmaceutical composition includes a calcium antagonist agent.

5. A method as claimed in claim 4, wherein said calcium antagonist agent is nifedipine.

6. A method as claimed in claim 4, wherein said calcium antagonist agent is verapamil.

7. A method as claimed in claim 1, wherein said pharmaceutically-acceptable carrier comprises a coating around said magnesium compound.

8. A method as claimed in claim 7, wherein said coating consists of a material selected from the group consisting of a wax, a fatty acid, a fatty alcohol and an ester.

9. A method as claimed in cliam 7, wherein said coating consists of a material selected from the group consisting of hydrogenated castor oil, glyceryl monostearate, glyceryl distearate, 12-hydroxystearly alcohol and microcrystalline wax.

10. A method as claimed in claim 1, wherein the amount of said pharmaceutical composition orally administered provides 5 to 30 milligram equivalents of magnesium.

11. A method as claimed in claim 10, wherein the amount of said pharmaceutical composition orally administered provides 5 to 10 milligram equivalents of magnesium.

12. A method of treating a human patient suffering from magnesium/potassium deficiency, said method comprising the step of orally administering to such human patient a therapeutically meaningful dosage of a pharmaceutical composition which consists essentially of a magnesium compound selected from the group consisting of magnesium oxide, magnesium hydroxide and a pharmaceutically-acceptable salt of magnesium; a cardiac glycoside agent; and a pharmaceutically-acceptable carrier; said pharmaceutically-acceptable carrier functioning to control the release of magnesium into the digestive tract of said human patient over a period of from 2 to 24 hours.

13. A method of treating a human patient suffering from magnesium/potassium deficiency, said method comprising the step of orally administering to such human patient a therapeutically meaningful dosage of a pharmaceutical composition which consists essentially of a magnesium compound selected from the group consisting of magnesium oxide, magnesium hydroxide and a pharmaceutically-acceptable salt of magnesium; an adrenegic receptor blocking agent; and a pharmaceutically-acceptable carrier; said pharmaceutically-acceptable carrier functioning to control the release of magnesium into the digestive tract of said human patient over a period of from 2 to 24 hours.

* * * * *

UNITED STATES PATENT AND TRADEMARK OFFICE
CERTIFICATE OF CORRECTION

PATENT NO. : 4,788,180
DATED : November 29, 1988
INVENTOR(S) : Maurice Bloch

It is certified that error appears in the above-identified patent and that said Letters Patent is hereby corrected as shown below:

Column 1, line 28, after "with" insert --magnesium--

Column 2, line 10, change "hypokalaemia" to --hypocalcaemia--

Column 3, line 42, change "etc)" to --etc.--

Column 5, line 39, change "angine" to --angina--

Column 5, line 59, change "carrying" to --varying--

Column 9, line 40, change "hydrochlorotiazide" to --hydrochlorothiazide--

Column 9, line 41, change "bumeanide" to --bumetanide--

Column 10, line 29, change "cliam" to --claim--

Signed and Sealed this

First Day of August, 1989

*Attest:*

DONALD J. QUIGG

*Attesting Officer*  *Commissioner of Patents and Trademarks*